(12) United States Patent
Newton (10) Patent No.: US 8,723,109 B2
(45) Date of Patent: May 13, 2014

(54) DUAL SOURCE MASS SPECTROMETRY SYSTEM

(75) Inventor: Anthony Newton, Cheshire (GB)

(73) Assignee: Micromass UK Limited, Manchester (GB)

( * ) Notice: Subject to any disclaimer, the term of this patent is extended or adjusted under 35 U.S.C. 154(b) by 127 days.

(21) Appl. No.: 13/202,645

(22) PCT Filed: Mar. 8, 2010

(86) PCT No.: PCT/GB2010/050392
§ 371 (c)(1),
(2), (4) Date: Oct. 26, 2011

(87) PCT Pub. No.: WO2010/100508
PCT Pub. Date: Sep. 10, 2010

(65) Prior Publication Data
US 2012/0097844 A1 Apr. 26, 2012

Related U.S. Application Data (60) Provisional application No. 61/184,918, filed on Jun. 8, 2009.

(30) Foreign Application Priority Data

Mar. 6, 2009 (GB) .................................. 0903914.0

(51) Int. Cl.
*H01J 49/10* (2006.01)
(52) U.S. Cl.
USPC ...................................... 250/288; 250/423 R
(58) Field of Classification Search
USPC ...................... 250/288, 282, 423 R
See application file for complete search history.

(56) References Cited

U.S. PATENT DOCUMENTS

| 6,646,257 | B1 | 11/2003 | Fischer et al. | |
|---|---|---|---|---|
| 2008/0048107 | A1* | 2/2008 | Mcewen | 250/282 |
| 2008/0296485 | A1 | 12/2008 | Benter et al. | |
| 2012/0097844 | A1* | 4/2012 | Newton | 250/288 |
| 2012/0104246 | A1* | 5/2012 | Newton | 250/288 |
| 2012/0126108 | A1* | 5/2012 | Newton | 250/282 |

FOREIGN PATENT DOCUMENTS

| JP | 2004130263 | 1/1992 |
|---|---|---|
| JP | 2006215729 | 5/1994 |
| JP | 2004342620 | 2/2004 |
| WO | 2009137463 | 11/2009 |

OTHER PUBLICATIONS

International Search Report for application No. PCT/GB2010/050391, mailing date of Jul. 6, 2010, 7 pages.

(Continued)

*Primary Examiner* — Nikita Wells
*Assistant Examiner* — Johnnie L Smith
(74) *Attorney, Agent, or Firm* — Waters Technologies Corp.

(57) ABSTRACT

In or for a dual source mass spectrometry system (10), an ion source housing (16) for detachable connection to a mass spectrometer of the system. The ion source housing comprises a source chamber (22) having an outlet port for connection to a vacuum region of a mass spectrometer, a sample port for receiving a gas chromatography [GC] column and means for charging analyte molecules discharged from said GC column, wherein the housing comprises a docking means by which a GC interface probe can be releasably engaged with the housing.

3 Claims, 8 Drawing Sheets

(56) References Cited

OTHER PUBLICATIONS

International Written Report for application No. PCT/GB2010/050391, mailing date of Jul. 6, 2010, 8 pages.
International Search Report for application No. PCT/GB2010/050392, mailing date of Jul. 6, 2010, 7 pages.
International Written Report for application No. PCT/GB2010/050392, mailing date of Jul. 6, 2010, 8 pages.
International Search Report for application No. PCT/GB2010/050393, mailing date of Jul. 6, 2010, 7 pages.
International Written Report for application No. PCT/GB2010/050393, mailing date of Jul. 6, 2010, 8 pages.
Jeol Ltd; Interruption Control Method and Circuit for Analysis Apparatus, Journal of Technical Disclosure No. 2004-500966, Publication Date: Feb. 18, 2004, pp. 4.
Translation of Notice of Rejection (Official Action), for Japanese Patent Application No. 2011-552530, Mailing Date: Jan. 28, 2014, pp. 2.

* cited by examiner

DUAL SOURCE MASS SPECTROMETRY SYSTEM

BACKGROUND OF THE INVENTION

1. Field of the Invention

The present invention is directed generally to scientific laboratory analytical equipment, and more particularly, to the combination of Chromatography Systems and Mass Spectrometers.

2. Background of the Related Art

Scientific laboratories commonly need to analyse samples by the use of Chromatography in order to separate different constituents within the samples. Once the samples have been separated, they may need further analysis in order to identify what the different constituents are. Normally the most effective way of performing the analysis of the separated constituents is the use of mass spectrometers.

Chromatography can be performed either on gaseous samples or on liquid samples. However, the apparatus required to perform Liquid Chromatography and Gas Chromatography are rather different, so much so that different machines are required to perform the different analyses.

Mass spectrometers can be used to measure the mass of ions and analyse the structure of these ions, by studying fragmentation of the ions that may occur within the mass spectrometer. Chromatography systems typically produce molecules rather than ions, so the mass spectrometer needs to produce ions from the molecules that are delivered to it. This typically is performed in an ion source. There are many ways of ionizing the molecules that are injected into an ion source. Atmospheric Pressure Chemical Ionisation [APCI] is one of these methods. In this method, the molecules are sprayed into an ion source chamber and the spray is subjected to a corona discharge that creates ions.

APCI is a desirable fragmentation technique because it typically produces singly charged ions, and so the results of the analysis are easier to interpret. Furthermore APCI is a method of ionization that is possible to use for samples that are both liquid and gaseous.

Mass Spectrometers are precise instruments, and so are expensive and delicate. Until recently, they have always been specifically designed for one of LCMS or GCMS and not for interchangable use. In the past also instruments have been designed to swap between GCMS and LCMS. However, the changeover has been time consuming and often the dual instruments compromised the performance on one or the other of the two techniques. This is especially true for Vacuum GCMS systems utilizing Electron Impact Ionization. The advantage of using APCI is that both LCMS and GCMS are operated at the same pressure and there is no need to change the MS other than to put an ion chamber on in place of a cone gas nozzle.

An attempt to provide a dual source mass spectrometry system comprises a mass spectrometer that has an ion source capable of being used for either LCMS or GCMS. However the design of the source is such that both an LCMS interface probe and a GCMS interface probe are permanently connected to an API source housing. This arrangement is an improvement over the use of separate LCMS and GCMS machines but is inefficient, and so cannot easily identify small quantities of analytes that may be present in the sample.

It would therefore be desirable to produce a Mass Spectrometer that is capable of efficiently analysing the output of either liquid or gas chromatography systems with easy transfer between the two different inputs, and with easy and minimal alterations required as now provided by the present invention.

It is envisaged that the dual source mass spectrometry system of the present invention has applications for example in synthetics confirmation and impurity profiling, natural products research, and in the fields of flavours and fragrances, nutraceuticals, petrochemicals, metabolomics, environmental screening, pesticide residue analysis and some forensic applications. The combination of LCMS and GCMS allows a wider range of compounds to be analyzed on a single instrument platform.

SUMMARY OF THE INVENTION

The present invention provides in or for a dual source mass spectrometry system, an ion source housing for detachable connection to a mass spectrometer of the system, the ion source housing comprising an ion source chamber having an outlet port for connection to a vacuum region of a mass spectrometer, a sample port for receiving a gas chromatography [GC] column and means for charging analyte molecules discharged from said GC column, wherein the housing comprises a docking means by which a GC interface probe can be releasably engaged with the housing.

According to a feature of the invention, a gas inlet may be provided for ingress of an inert gas into the chamber.

According to another feature of the invention, the docking means may comprise a docking nozzle in the housing to receive the GC interface probe and locking means provided by the nozzle for co-operation with complementary locking means provided by the GC interface probe by which the probe is progressively drawn into the docking nozzle and releasably locked in position. Preferably, the docking port comprises a screw-threaded nozzle incorporating sealing means whereby the probe is sealingly coupled with the nozzle.

DESCRIPTION OF THE DRAWINGS

An embodiment of the invention will now be described, by way of example, with reference to the accompanying drawings, in which.

SPECIFIC DESCRIPTION

Figure 1:
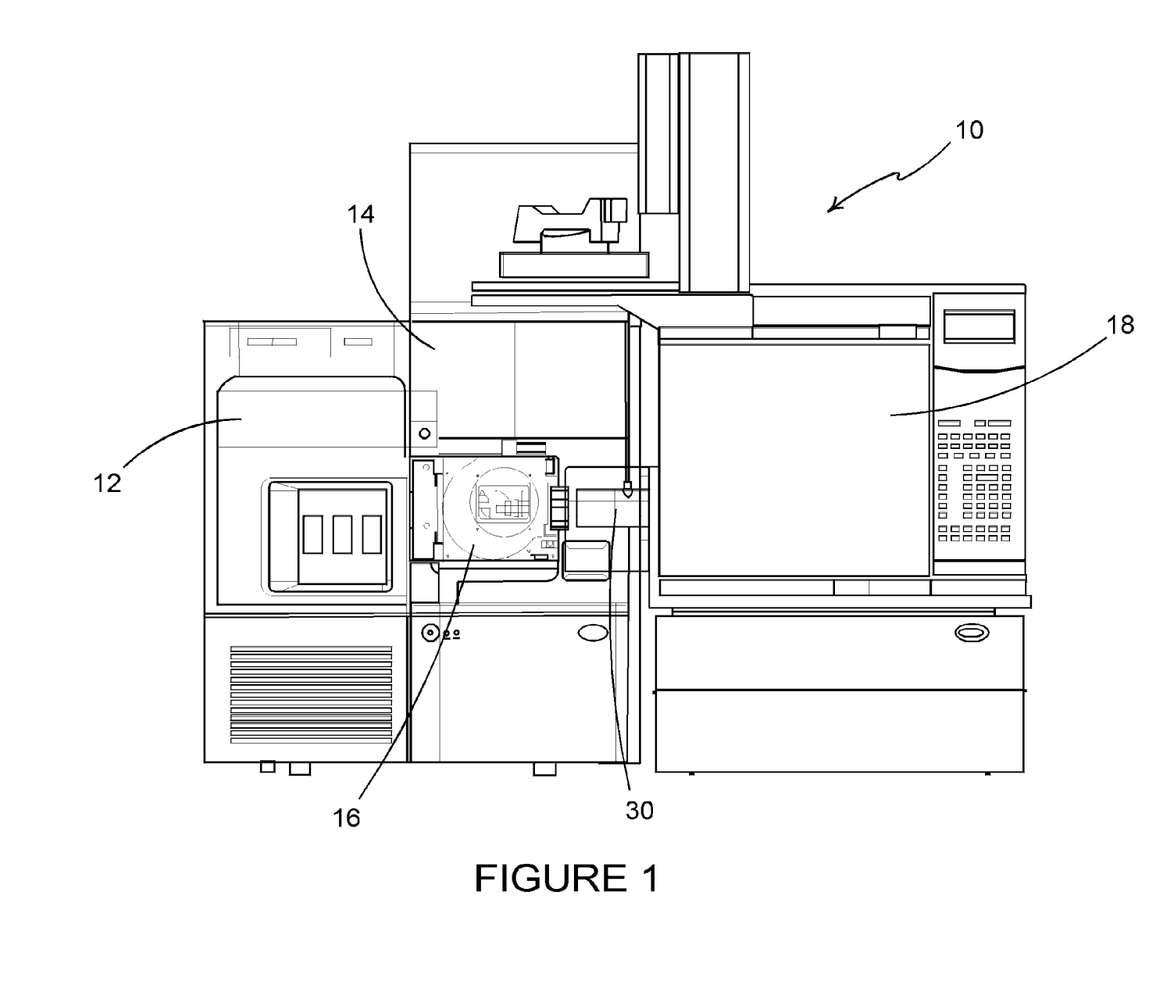
FIG. 1 is a perspective view of the dual source mass spectrometry system comprising an LC source unit, an MS unit and a GC unit.

Referring to the drawings there is shown a dual source mass spectrometry system 10 which comprises a liquid chromatography [LC] unit 12, a mass spectrometer [MS] unit 14, an ion source housing 16 which may be suitable for use with the LC unit or with the GC unit and a gas chromatography [GC] unit 18.

When it is required for the system to operate in LC/MS mode, the ion source housing 16 is one which is appropriate for use with a LC column of the LC unit 12 in which case the GC unit 18 is disengaged and refracted from the MS unit 14. In order to operate the system in GC/MS mode, the LC ion source housing (not shown) is substituted by a GC ion source housing and the GC unit 18 is put into a deployed position in which it is operatively connected to the MS unit.

Figure 2:
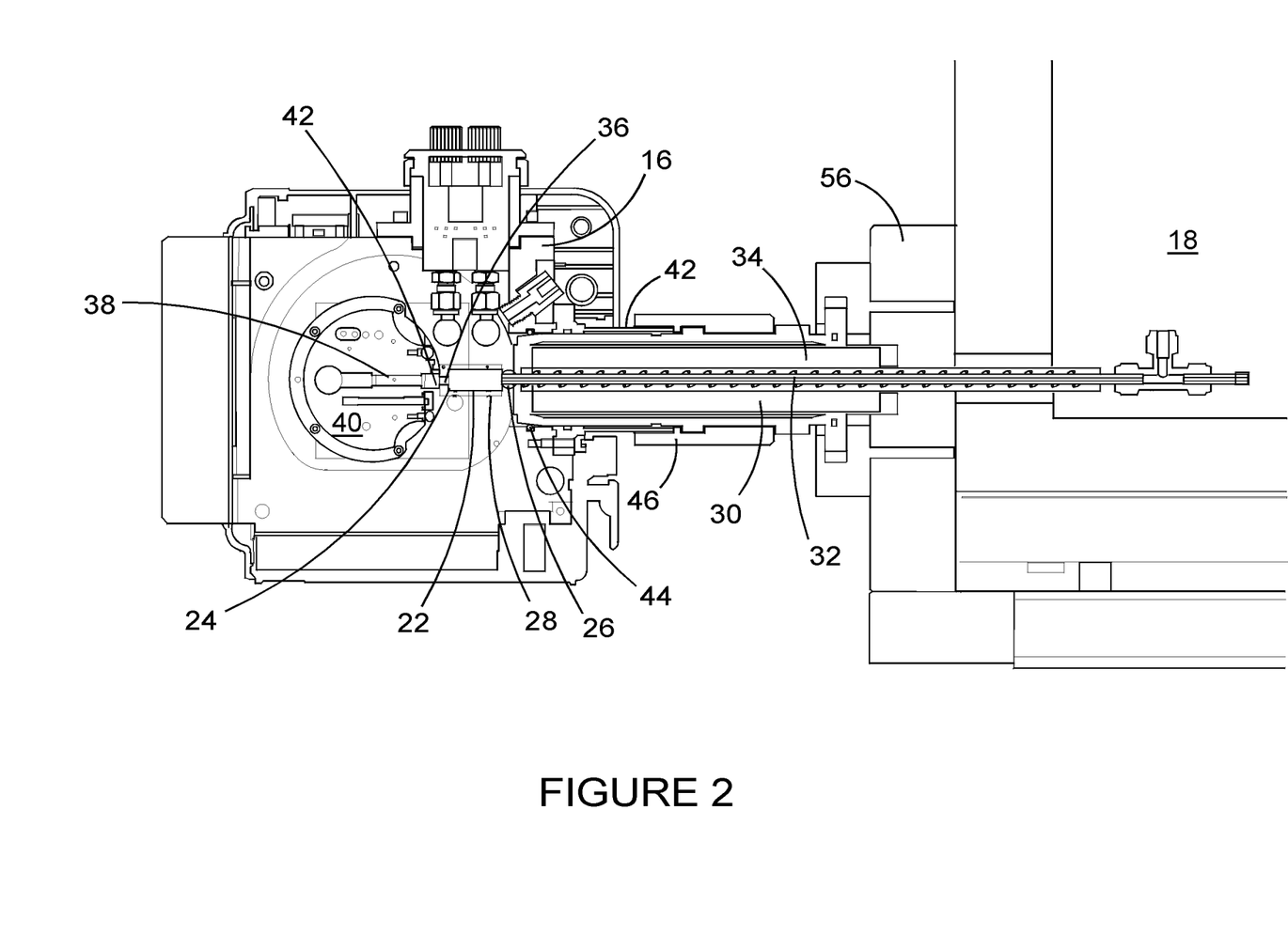
FIG. 2 is a cross-sectional view of the GC ion source housing and the GC interface probe.

Referring now to FIG. 2 of the drawings, the GC ion source housing 16 incorporates an ion source chamber 22. The chamber 22 has at least one outlet port 24, at least one gas inlet (not shown), a sample port 26, and at least one corona pin port 28.

The housing 16 is made of a structural material such as plastics, metal, glass or ceramic. A preferred metal is stainless steel, titanium, aluminium, copper, brass and other alloys.

The sample port 26 is constructed and arranged to receive a GC interface probe 30 comprising a gas chromatographic column 32. The column is surrounded by a heated sheath gas tube 34. The gas chromatographic column 32 is for placing the analyte molecules in the chamber 22. The analyte molecules are suspended or dissolved in gas. The column has a mobile phase and a stationary phase and is used to separate components based upon their vapour pressure. When compounds elute from the column into the chamber they are in the vapour phase. Gas chromatographic columns are known in the art and are available from several venders. For example, without limitation, gas chromatographic columns are sold by Varian, Inc. (Palo Alto, Calif., USA) under several trademarks including FactorFour™, CP-Sil, and Select™.

Figure 2A:
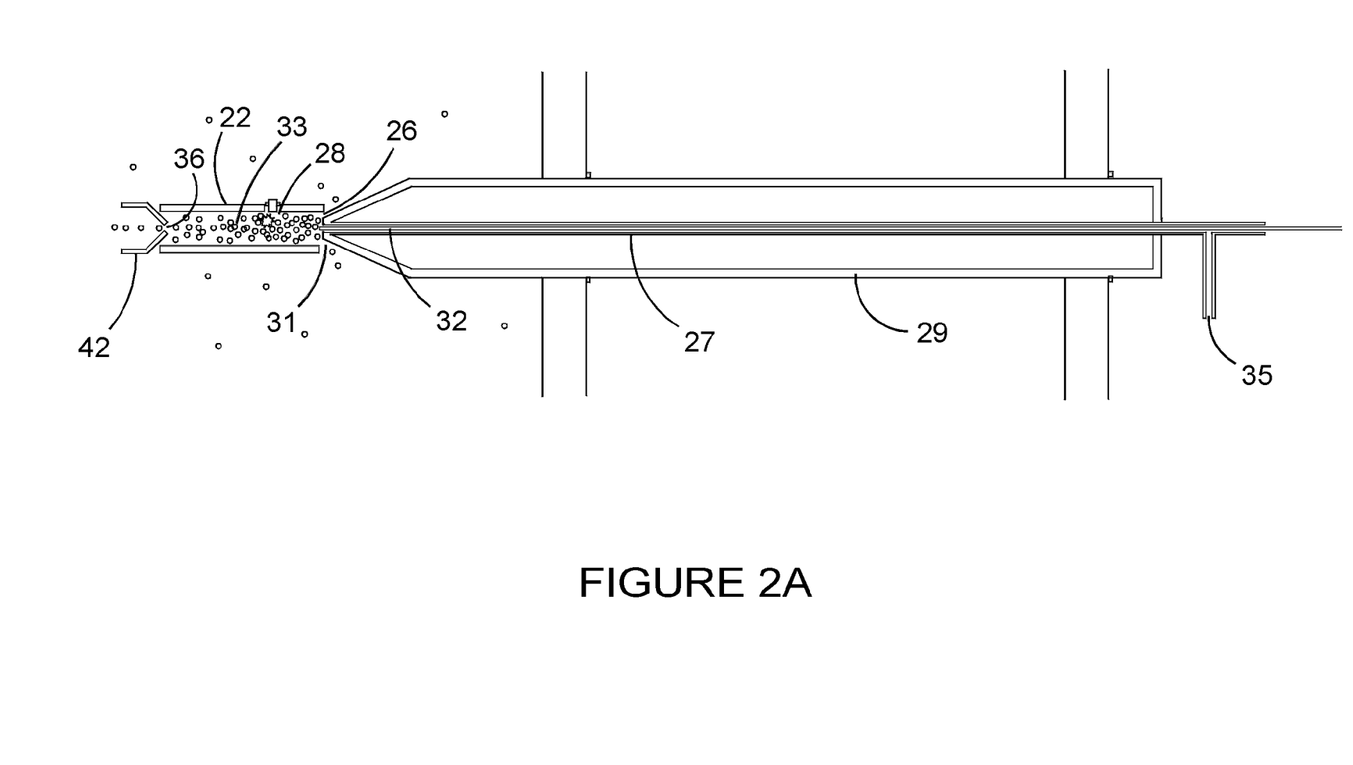
FIG. 2A is a schematic view of the GC transfer line showing the ion source enclosure or housing and the GC oven in the GC unit.

Referring to FIG. 2A, the sample port 26 receives the inner tube 27 of a transfer line 29 and transfer line tip 31 from which the column 32 protrudes. It is not a close fit but has a reasonable clearance with the transfer line to prevent the chamber from grounding on the metal transfer line. The outside wall of the column 32 and the inner diameter of the sample port cooperate to form a close fit. However, the fit need not be airtight. A gap allows excess gas in chamber 22 to vent and be carried off by a vent structure of the atmospheric pressure ionization housing. Thereby the chamber is swept out in the timescale of a chromatographic peak.

The gas inlet is constructed and arranged to be placed in fluid communication with a source of an inert gas [not shown] for placing the inert gas into the chamber 22. Inert gases comprise any substantially non-reactive gas, such as nitrogen. Such gases are sold by numerous venders under pressure in tanks.

The outlet port 24 is constructed and arranged to be received on or about an opening 36 of a vacuum region 38 of a mass spectrometer generally designated by the numeral 40. The opening 36 normally interfaces between the vacuum region 38 and an atmospheric pressure region of the atmospheric pressure ionization housing 16. The atmospheric region may deviate slightly from atmospheric but is substantially near atmospheric pressure.

Opening 36 is formed in an inlet cone 42 which substantially fills the outlet port 24 to form a substantially closed chamber 22. The chamber 22 has a volume of 0.5 to 5.0 cc when the outlet port 24 is received on or about the opening 36 of the vacuum region 38.

The opening 36 of the vacuum region 38 defines a sample axis. A preferred sample port 24 is constructed and arranged to introduce analyte molecules 33 within sixty degrees of a line perpendicular to the sample axis.

The corona pin port 28 is constructed and arranged for receiving a corona discharge pin for discharging electrons. The discharged electrons place a charge on analyte molecules 33 (FIG. 2) as the analyte molecules leave the gas chromatographic column 32. These charged and uncharged analyte molecules are circulated around the chamber 22 by the gas introduced through the gas inlet and received in the opening 36 of the vacuum region for mass analysis.

Preferably, the corona discharge port is constructed and arranged to place the corona discharge pin within the flow of the sample discharged from the gas chromatographic column 32. Usually, the corona discharge port is aligned with the sample axis allowing gases to circulate around the corona discharge pin. Plasma formed by corona discharge into a gas consists of the carrier gas in combination with make-up gas supplied through the transfer inner tube 27 through a connecting line 35.

In the case of N2 make-up gas N2$^+$ and N4$^+$ are formed in the plasma then

N2$^+$+M>M$^+$.+N2

N4$^+$+M>M$^+$.+2N2

In addition with trace amounts of moisture H30$^+$, then

H30$^+$+M>MH$^+$+H20

With higher concentrations of water H$^+$(H20)$_n$, then

H$^+$(H20)$_n$+M>MH$^+$+$n$H20

Selective ionization can also be performed by photo-ionization.

The removal of the GC ion source housing 16 allows the mass spectrometer to receive liquid samples from an LC atmospheric pressure ionization source [not shown] in a conventional manner.

Figure 3:
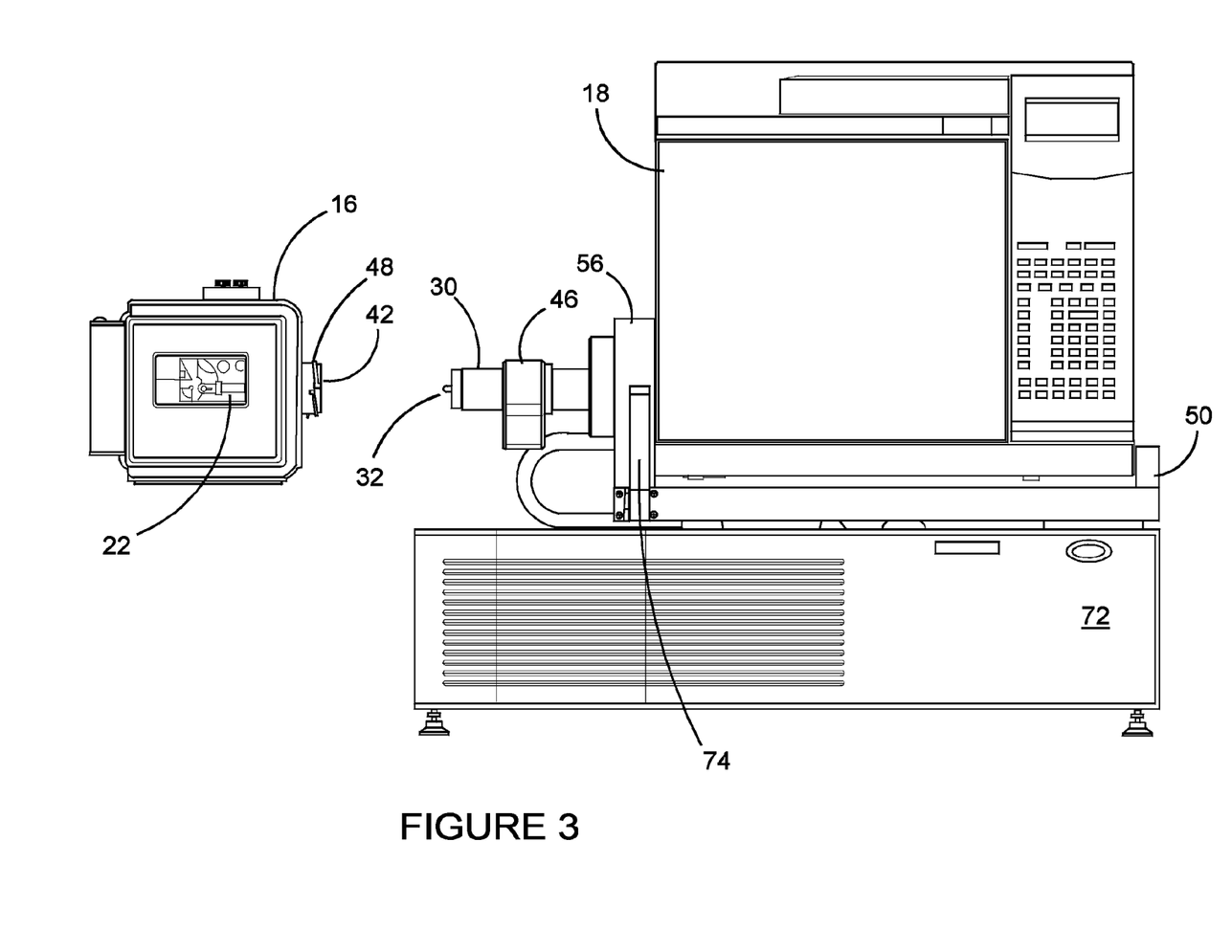
FIG. 3 is a perspective view of the GC unit and the GC ion source housing with the GC interface probe in a refracted position.
Figure 4:
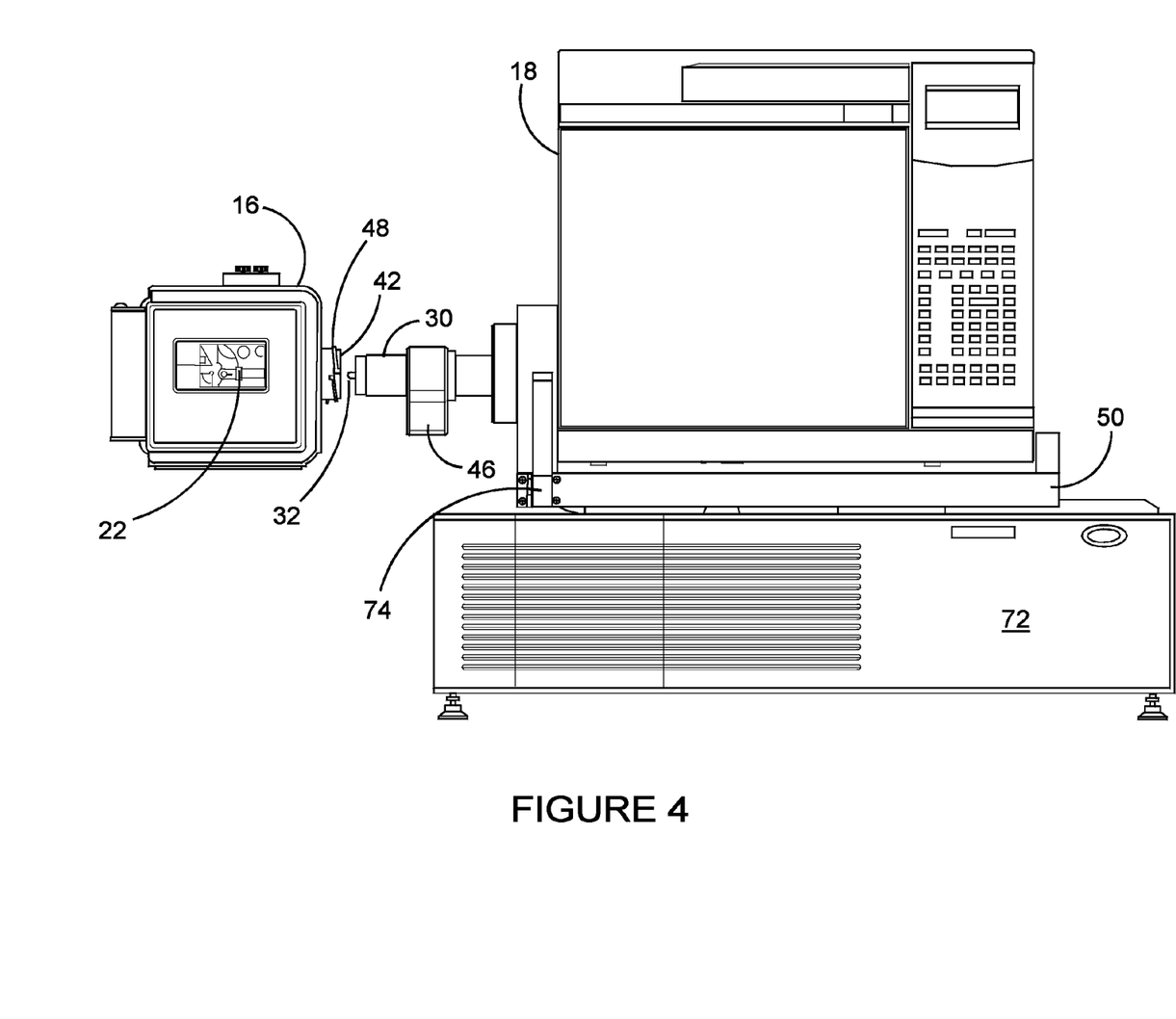
FIG. 4 is a view similar to FIG. 3 but showing the GC interface probe offered up to the GC ion source housing.

Referring to FIGS. 2, 3 and 4, the GC ion source housing 16 includes a nozzle 42 which forms part of complementary docking means for detachably receiving the GC interface probe 30 which incorporates the GC column 32. The nozzle includes a sealing O-ring 44 (FIG. 2) by which the GC interface probe is sealingly engaged in the nozzle. Referring back to FIGS. 3 and 4, the GC interface probe 30 has another part of the complementary docking means which includes a rotatable screw-threaded locking lever 46 which co-operates with a mating screw-threaded portion 48 of the docking nozzle such that when the probe is offered up to the nozzle, engagement of the complementary screw-threaded parts by manipulation of the locking level causes the probe, and hence the GC column, to be progressively docked in the chamber 22 of the GC ion source housing 16.

Figure 5:
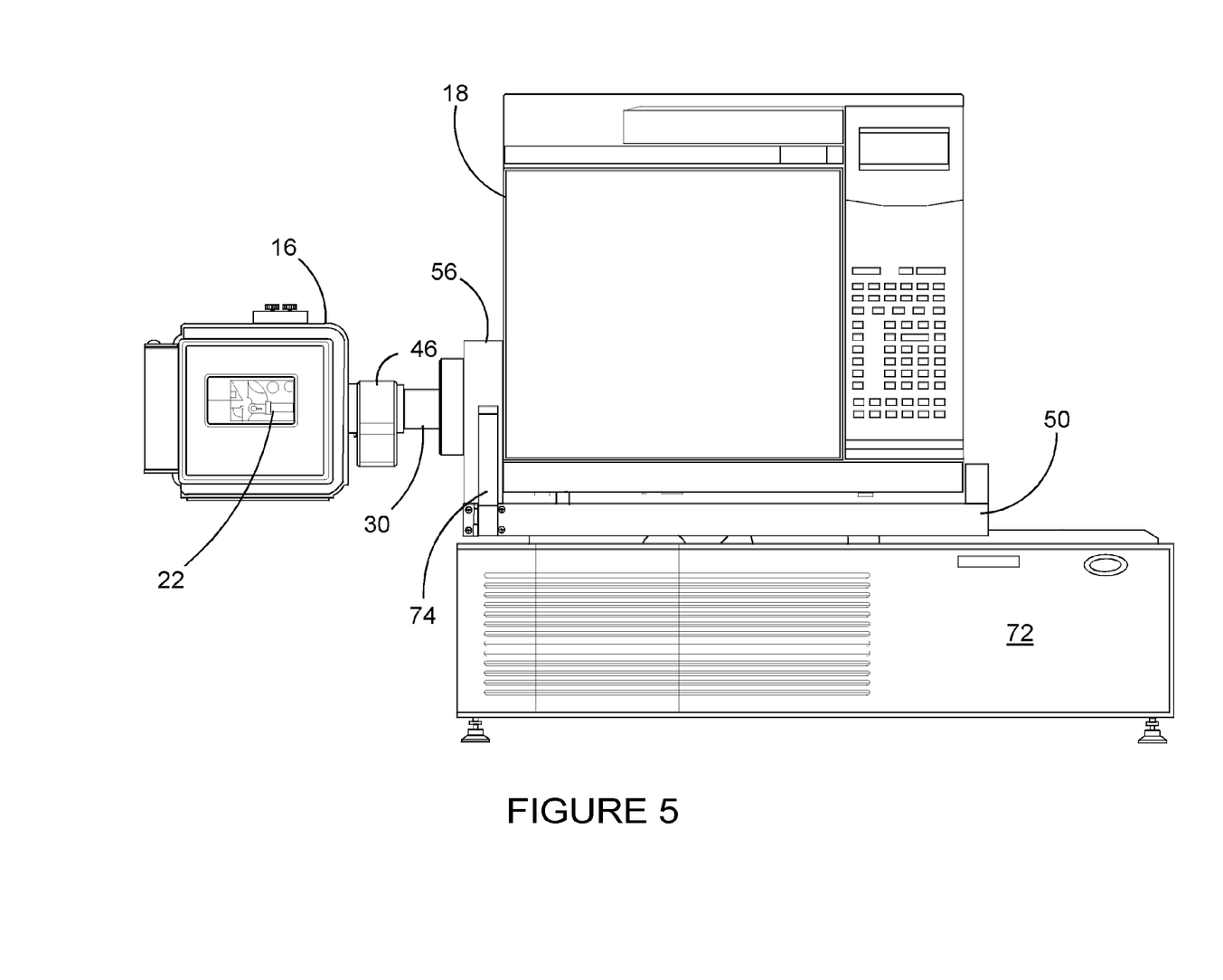
FIG. 5 is a view similar to FIG. 4 but showing the GC interface probe engaged with the GC ion source housing in a deployed position.

In order to take the GC interface probe 30 from a retracted position in which it is disengaged from the GC ion source chamber, whereby the system is operable in a first LC/MS mode, into a deployed position in which the GC interface probe 30 is operatively connected to the GC ion source chamber, whereby the system is operable in a second GC/MS mode, as shown in FIG. 5, the GC unit is slidably mounted on a rail system.

Figure 6:
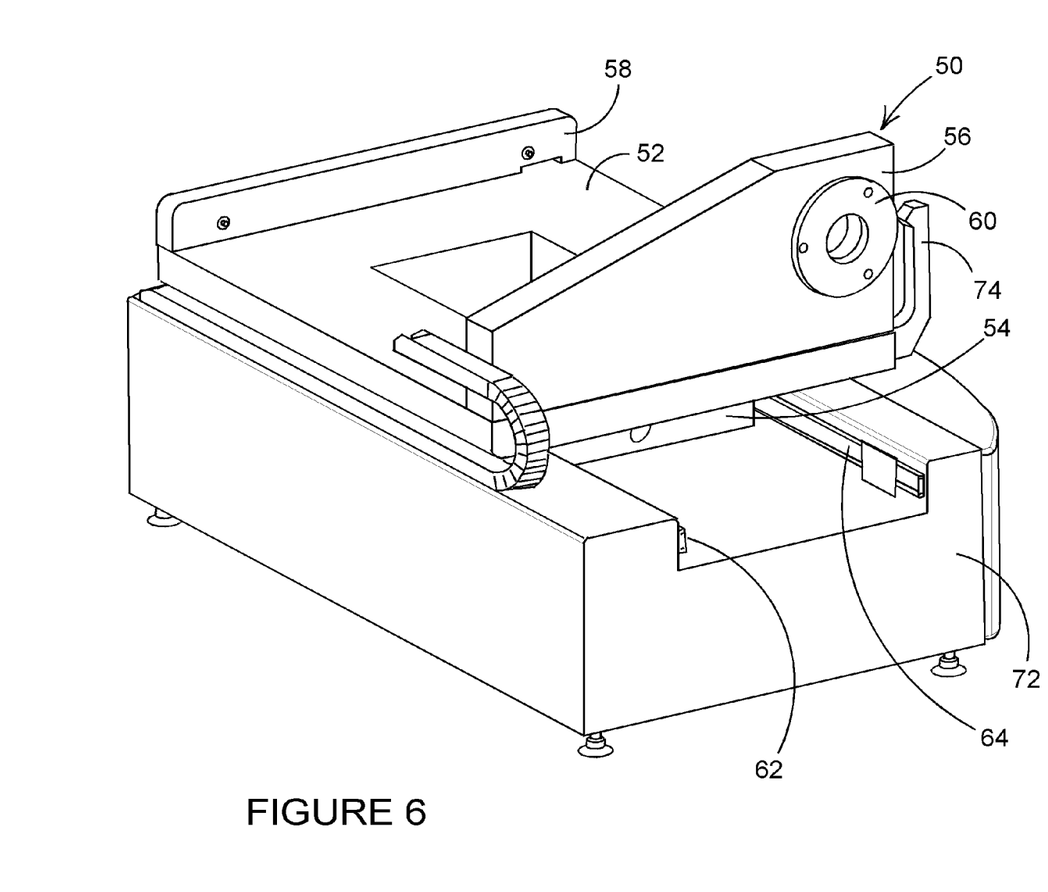
FIG. 6 is a perspective view of a slidable carriage which receives the GC unit and is mounted on rails to a base unit.
Figure 7:
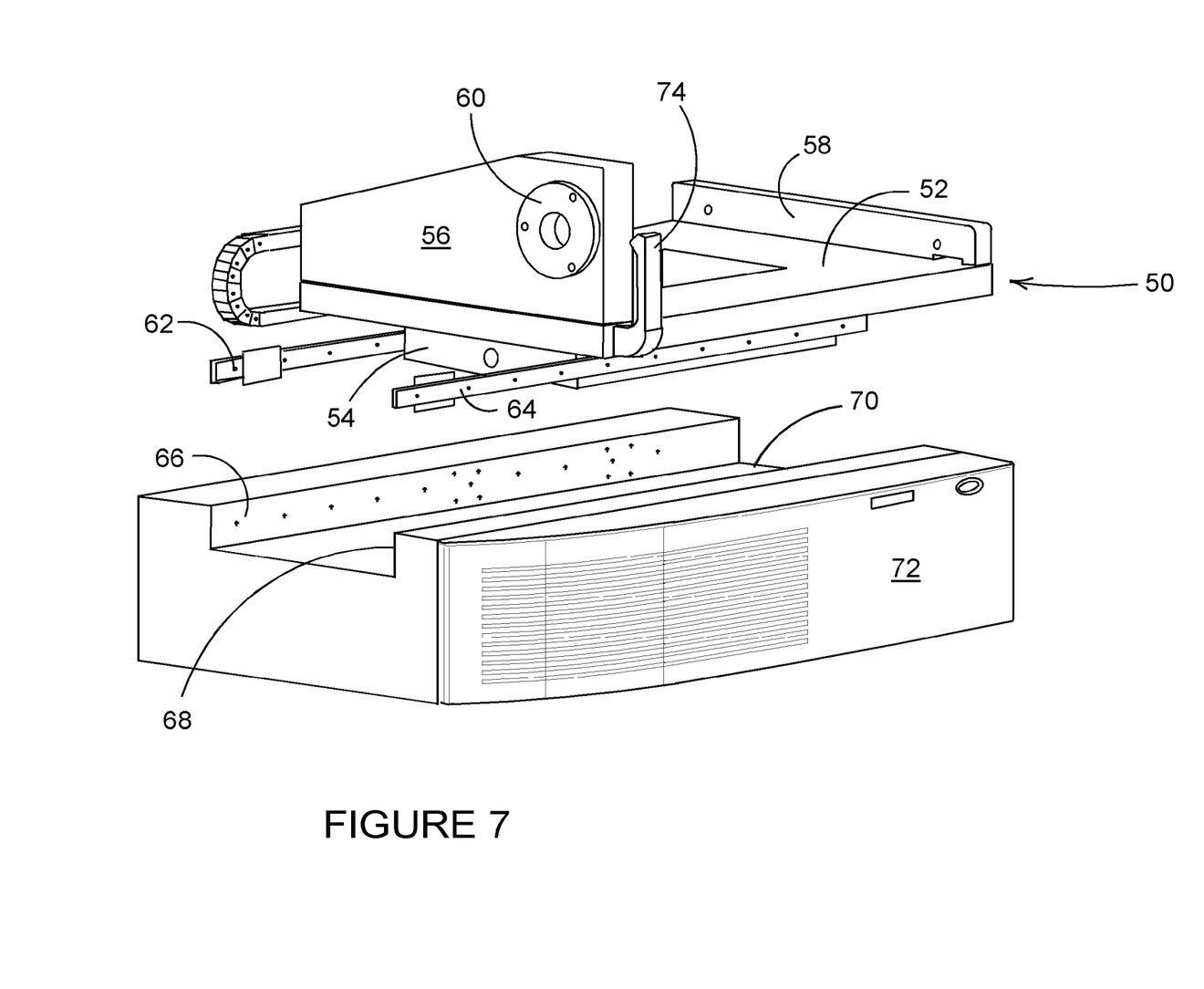
FIG. 7 is an exploded perspective view of the carriage, rail system and base unit.

Referring now to FIGS. 6 and 7 of the drawings, details of the GC unit rail system are shown. The GC unit 18 (see FIGS. 1 to 5) is received in a carriage 50 which includes a floor 52 having a keel portion 54 and end walls 56, 58 respectively by which the GC unit 18 is secured to the carriage 50. End wall 56 includes an opening 60 through which the GC interface probe extends from the GC unit. The keel portion 54 is furnished with a pair of parallel rails 62, 64 (which operate in a manner similar to those found in office filing cabinets) which have runners fixed to opposed walls 66, 68 of a channel 70 formed in the upper face of a base unit 72 so that the keel portion sits with clearance in the channel. Thus the carriage (together with the GC unit 18) can slide to and fro with respect to the base unit. A locking handle 74 is provided by the carriage to assist in the sliding movement of the carriage but also for manipulation to lock the rail 66 against the channel to prevent movement of the carriage relative to the base unit.

The travel of the carriage relative to the base unit is such that when the GC unit is retracted, the GC transfer probe is drawn clear of the MS unit and, at the extremity of its travel in the opposite direction, the GC transfer probe is presented to the docking nozzle so that the complementary docking means can progressively draw in the probe and hence the GC column for operative connection to the chamber.

The invention claimed is:

1. An ion source housing for a dual source mass spectrometry system, the ion source housing for detachable connection of a gas chromatography interface probe to a mass spectrometer of the system, the ion source housing comprising an ion source chamber having an outlet port for connection to a vacuum region of a mass spectrometer, a sample port for receiving a gas chromatography [GC] column and means for charging analyte molecules discharged from said GC column, wherein the housing comprises a docking means by which a GC interface probe can be releasably engaged with the housing, the docking means comprising (i) a docking nozzle in the housing to receive the GC interface probe and (ii) locking means provided by the nozzle for co-operation with complementary locking means provided by the GC interface probe by which the probe is progressively drawn into the docking nozzle and releasably locked in position.

2. An ion source housing as claimed in claim 1, further comprising a gas inlet for ingress of an inert gas into the chamber.

3. An ion source housing according to claim 1, wherein the docking port comprises a screw-threaded nozzle incorporating sealing means whereby the probe is sealingly coupled with the nozzle.

* * * * *